US007645225B2

(12) United States Patent
Medvedev et al.

(10) Patent No.: US 7,645,225 B2
(45) Date of Patent: Jan. 12, 2010

(54) CHRONIC PERFORMANCE CONTROL SYSTEM FOR ROTODYNAMIC BLOOD PUMPS

(76) Inventors: Alexander Medvedev, 4304 Lander Rd., Orange Village, OH (US) 44022; Leonard A. R. Golding, 16650 Auburn Rd., Auburn Road, OH (US) 44026; Alexander Massiello, 10340 Wye Rd., Chesterland, OH (US) 44026

( * ) Notice: Subject to any disclaimer, the term of this patent is extended or adjusted under 35 U.S.C. 154(b) by 315 days.

(21) Appl. No.: 10/333,759

(22) PCT Filed: Mar. 19, 2001

(86) PCT No.: PCT/US01/08776

§ 371 (c)(1),
(2), (4) Date: Apr. 1, 2004

(87) PCT Pub. No.: WO01/72352

PCT Pub. Date: Oct. 4, 2001

(65) Prior Publication Data

US 2004/0152944 A1    Aug. 5, 2004

Related U.S. Application Data

(60) Provisional application No. 60/192,221, filed on Mar. 27, 2000.

(51) Int. Cl.
*A61M 1/12* (2006.01)
(52) U.S. Cl. .................... 600/17; 600/16; 623/3.1; 623/3.28; 417/44.1; 417/44.11; 318/432; 318/438
(58) Field of Classification Search .................... 600/16, 600/17; 623/3.1, 3.28; 417/44.1, 44.11; 318/432, 438
See application file for complete search history.

(56) References Cited

U.S. PATENT DOCUMENTS 5,271,395 A * 12/1993 Wahlstrand et al. ............ 607/9

(Continued)

FOREIGN PATENT DOCUMENTS

| JP | 08-270595 | 10/1996 |
|----|-----------|---------|
| JP | 10-085322 | 7/1998  |

OTHER PUBLICATIONS

Vollkron, PhD, Michael; Voitl, JD, Peter; TA, Julia; Wieselthaler, MD, Georg; and Schima, PhD, Heinrich; "Suction Events During Left Ventricular Suport and Ventricular Arrhythmias", International Society for Heart and Lung Transplantation, Aug. 2007, pp. 819-825.
Vollkron, PhD, Michael; Schima, PhD, Heinrich; Huber, Leopold; Benkowski, Robert; Gino Morello; and Weiselthalter, Georg; "Development of a Suction Detection systemfor Axial Blood Pumps", International Center for Artificial Organs and Transplantation, 2004, pp. 709-716; Blackwell Publishing, Inc.

*Primary Examiner*—Carl H Layno
*Assistant Examiner*—Paula J Stice
(74) *Attorney, Agent, or Firm*—Amster, Rothstein & Ebenstein LLP

(57) ABSTRACT

In a left ventricular assist device (LVAD) a rotodynamic blood pump (10) is powered by a brushless DC motor (12). A power supply (14) supplies power to the motor (12). Three feedback channels, one for each of voltage, current, and motor speed lead to a microcontroller or microprocessor (18). The three feedback waveforms are analyzed, and from these waveforms, motor input power, patient heart rate, current pump flow rate, and systemic pressure are determined. The microprocessor (18) then calculates a desired flow rate proportional to the patient heart rate. The microprocessor communicates a new power output to a commutation circuit (16), which regulates power to the motor (12). The pump (10) also includes safety checks that are prioritized over desired pump flow. These include prevention of ventricular suction, low pulsatility, minimum and maximum pump speed, minimum speed-relative pump flow, minimum absolute pump flow, minimum and maximum motor input power.

24 Claims, 8 Drawing Sheets

U.S. PATENT DOCUMENTS

| | | | |
|---|---|---|---|
| 5,324,177 A * | 6/1994 | Golding et al. | 417/423.1 |
| 5,711,753 A * | 1/1998 | Pacella et al. | 600/16 |
| 5,725,357 A * | 3/1998 | Nakazeki et al. | 417/18 |
| 5,879,375 A * | 3/1999 | Larson et al. | 607/30 |
| 5,888,242 A * | 3/1999 | Antaki et al. | 623/3.28 |
| 5,924,975 A * | 7/1999 | Goldowsky | 600/16 |
| 5,947,892 A * | 9/1999 | Benkowski et al. | 600/16 |
| 5,965,089 A * | 10/1999 | Jarvik et al. | 422/44 |
| 6,048,363 A * | 4/2000 | Nagyszalanczy et al. | 623/3.13 |
| 6,135,943 A * | 10/2000 | Yu et al. | 600/16 |
| 6,162,167 A * | 12/2000 | Goldstein et al. | 600/16 |
| 6,183,412 B1 * | 2/2001 | Benkowski et al. | 600/16 |
| 6,572,530 B1 * | 6/2003 | Araki et al. | 600/17 |
| 7,004,924 B1 * | 2/2006 | Brugger et al. | 604/6.13 |
| 2005/0215843 A1 * | 9/2005 | Medvedev | 600/16 |

* cited by examiner

_US 7,645,225 B2_

CHRONIC PERFORMANCE CONTROL SYSTEM FOR ROTODYNAMIC BLOOD PUMPS

CROSS REFERENCE TO RELATED APPLICATION

This is a U.S. National Phase Application of PCT/US01/08776, filed Mar. 19, 2001, which claims the benefit of U.S. Provisional Application No. 60/192,221, filed Mar. 27, 2000.

FEDERAL RESEARCH STATEMENT

The U.S. Government may have certain rights in this invention pursuant to contract number N01-HV-58159 awarded by the U.S. National Heart, Lung and Blood Institute of the National Institutes of Health

BACKGROUND OF THE INVENTION

The present invention relates to the medical arts. It finds particular application in cardiac assist technologies using, for example, rotodynamic blood pumps, also known as left ventricular assist devices (LVAD) in assisting patients with failing hearts and will be described with particular reference to a centrifugal blood pump. It is to be appreciated that the present invention is also applicable to other types of pumps, such as axial flow pumps, and is not limited to the aforementioned application.

Electrically driven rotodynamic pumps (axial flow, mixed flow and centrifugal) have prospective applications in cardiac assist technologies. A typical cardiac assist system includes the blood pump itself, electrical motor (usually a brushless DC motor integrated into the pump), drive electronics, microprocessor control unit, and an energy source, such as rechargeable batteries. These pumps are used in fully implantable systems for chronic cardiac support. In this case the whole system is located inside the body and there are no drive lines penetrating the skin. For temporary support, and as well as for the bridge-to-transplant application, the pump itself is also located inside the body. However some system components including drive electronics and energy source may be placed outside the patient body.

Both chronic and temporary patient support require controlling the pump performance to satisfy the physiologic needs of the patient while maintaining safe and reliable system operation.

The primary goal for cardiac assist control is to provide an adequate blood pump flow rate for the patient that may depend on various physiological and psychological factors. Prior systems have pressure sensors, or ECG sensors external to the pump to determine the heart rate and blood pressure of the patient. These systems require extra hardware inside the patient and increase the risk of complication.

U.S. Pat. No. 5,888,242 to Antaki et al. discloses a rotodynamic ventricular assist pump that uses current measurements and pump rotations per minute (rpm) measurements to test and identify a maximum rpm that will not cause ventricular collapse. The invention described in this patent monitors for a current spike indicative of ventricular collapse, and in response decreases the pump speed. It does this iteratively to achieve a maximum average flow rate. This approach puts unnecessary strain on the heart by continuously depending on this dangerous situation to optimize pump flow.

The present invention provides a new and improved method and apparatus that overcomes the above referenced problems and others.

SUMMARY OF THE INVENTION

In accordance with one aspect of the present invention, a cardiac assist device is provided. A blood pump is driven by a drive unit powered by a power supply. Three measurable parameters, current, voltage and rotational frequency (or pump speed) each relay their respective sensed waveforms to a controller. A motor winding commutation circuit directed by the controller directs power to the drive unit in response to the sensed waveform.

In accordance with another aspect of the present invention, a method of controlling blood flow with a blood pump is given. A current waveform, voltage waveform, and rotational frequency waveform, are sensed. The sensed information is provided to a blood pump controller which alters operation of the blood pump if necessary.

One advantage of the present invention is its independence of supply voltage variations.

Another advantage is that it uses a sensorless approach where no flow or pressure sensors are used.

Another advantage is simple control circuitry.

Another advantage is that it takes into account blood viscosity variations.

Yet another advantage resides in the enhanced control flexibility and precision while improving system reliability and effectiveness.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

There are several possible approaches to setting a required pump performance level matched to patient individual needs. A simple one employs a few levels of fixed pump speed/flows (i.e., low, medium, high) that are set according to patient activity (i.e., sleeping, sitting, walking). Another more flexible approach uses cardiac pacing technology where a separate pacemaker type device controls the pump performance. The present invention, though, proposes methods that employ patient systemic pressure and/or heart rate to define the required pump flow while using no pressure or ECG type sensors (so-called "sensorless" approach).

Studies have shown that there is an almost linear dependence between healthy human heart rate and cardiac output for different age groups and various activity levels. Therefore, maintaining an appropriate pump flow ($Q_{target}$) depending on the patient heart rate (HR) is a reasonable objective for the heart assist control algorithm.

Figure 1:
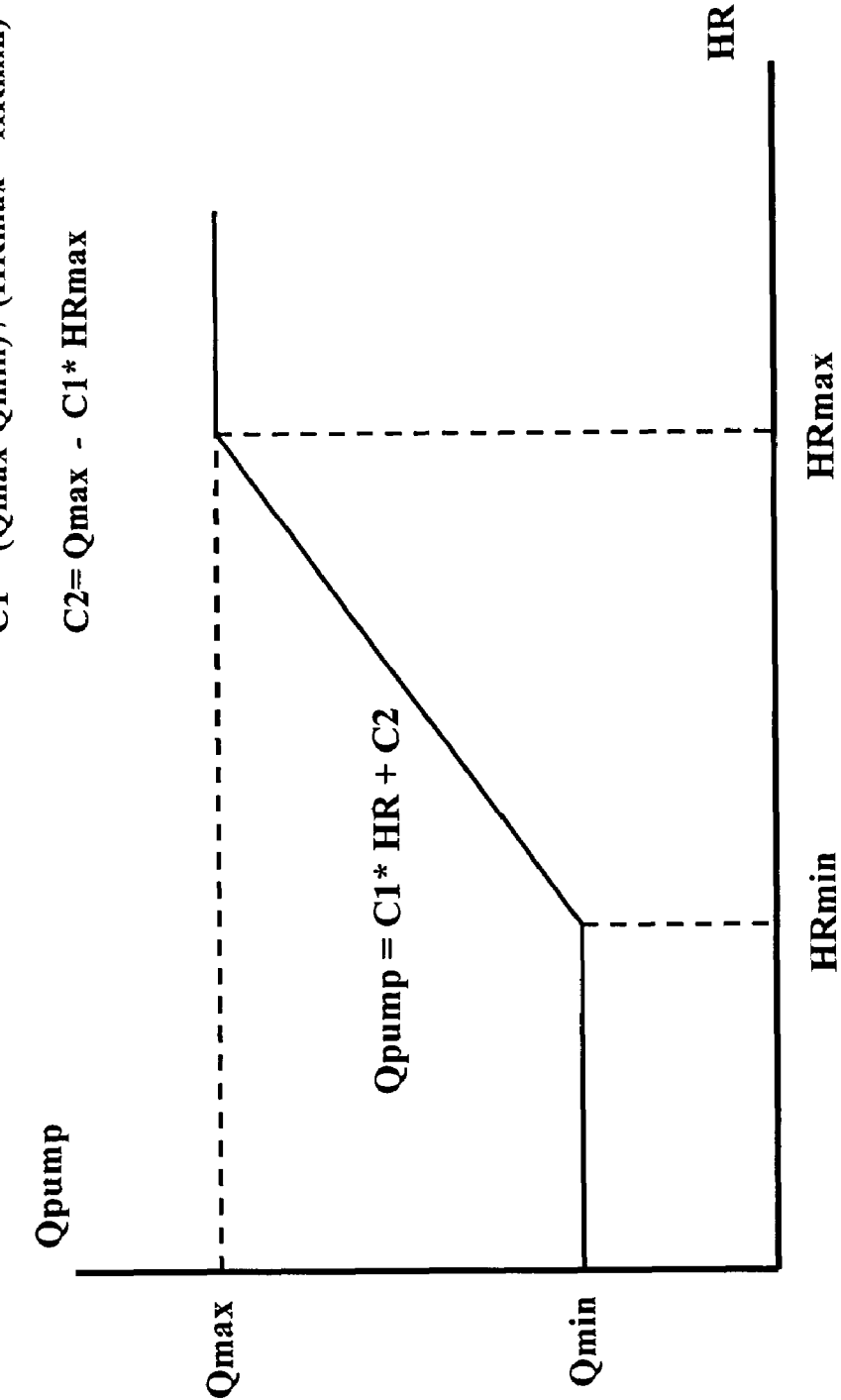
FIG. 1 is a graphical representation of targeted pump flow (Q) to heart rate (HR).

It is important that the controlled pump flow response to changes in patient HR be limited by a maximum (Qmax) and minimum (Qmin) allowed pump flow associated with upper (HRmax) and lower (HRmin) heart rate limits respectively. In other words, if HR>HRmax then $Q_{target}$=Qmax; if HR<Rmin then $Q_{target}$=Qmin. The values of Qmax, Qmin, HRmax and HRmin are based on the patient's residual ventricular function, body size and activity level. In the preferred embodiment (see FIG. 1.) the pump flow demand is proportional to the heart rate:

$$Q_{target}=C_1*HR+C_2, L/min. \quad (1)$$

where the constants $C_1$ and $C_2$ are found using following expressions:

$$C_1=(Q_{max}-Q_{min})/(HR_{max}-HR_{min})$$

$$C_2=Q_{max}-C_1*HR_{max}.$$

A linear dependence between the patient heart rate and the assisting pump flow rate is not the only possible relationship. There is some merit to an argument that the pump flow response can be a non-linear function. Generally, any equation that defines the required pump flow as a function of the patient heart rate can be used.

Figure 2:
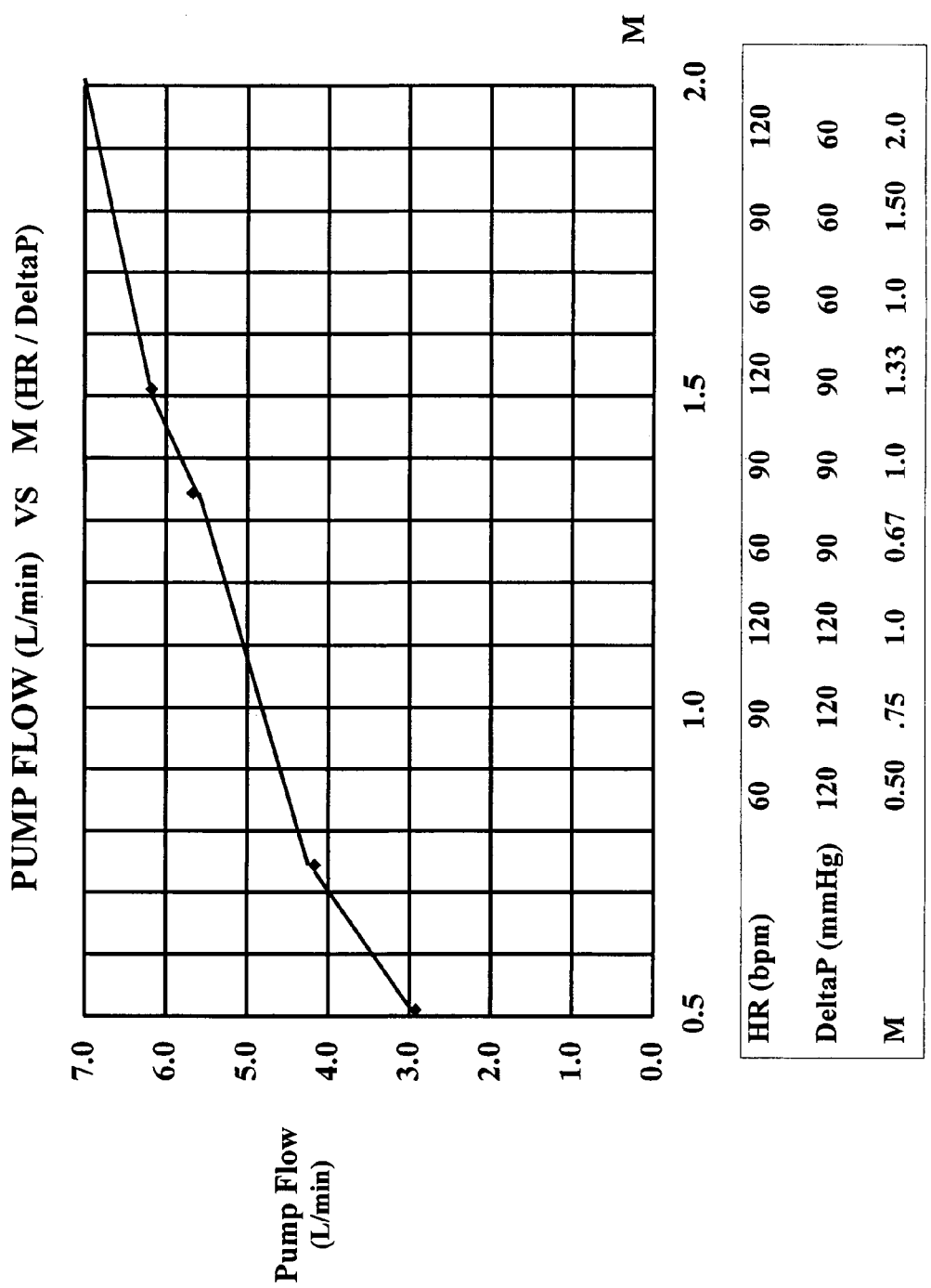
FIG. 2 is a graphical representation of targeted pump flow (L/min) versus a ratio (M) of heart rate (HR) and mean systemic pressure (P).

An alternate approach uses the patient heart rate and an estimated mean systemic pressure P to control the pump flow (see FIG. 2). The ratio M=HR/P is used as an independent variable that defines the appropriate pump flow:

$$Q_{target}=f(M). \quad (2)$$

where f is a monotonic function within the specified interval [Mmin, Mmax]. It is also important that the targeted pump flow response to changes in the M ratio be limited by maximum and minimum M values that are defined as follows:

$$Mmax=HRmax/Pmin;$$

$$Mmin=HRmin/Pmax.$$

Where Pmax and Pmin are upper and lower pressure limits respectively. In other words, if M>Mmax then $Q_{target}$=Qmax; if M<Mmin then $Q_{target}$=Qmin. Therefore, by setting Mmax and Mmin, a maximum and minimum pump flow response is defined. Again, the values of Qmax, Qmin, HRmax, HRmin as well as Pmax and Pmin are defined by the patient's residual ventricular function, body size and activity level. It is to be understood that any function that is monotonic within specified interval [$M_{min}$, $M_{max}$] can potentially be employed to define the required pump flow.

The relationship between pump flow and motor input power over a defined pump operating range can be obtained from the steady state power-flow characteristic for a particular pump type. Neglecting fluid inertia this relationship can be used to obtain instantaneous pump flow from a motor power waveform. Detection of motor power is both a safe and reliable control feedback for motors allowing determination of the instantaneous blood pump flow without direct measurement of flow or pressure drop across the pump. The detected instantaneous flow waveform can be employed to find the pump mean flow. The comparison of the target mean flow value derived from physiologic HR or HR/P input and the current calculated pump mean flow, results in an error signal used to change the pump performance in order to achieve the mean (target) blood flow.

When the rotodynamic blood pump is operated as an LVAD with ventricular cannulation, the motor power, current, speed and pump flow pulsatility correspond with the pulsatility of the ventricular pressure input into the pump inflow cannula. Thus, the heart rate may be found by analyzing the frequency components of the motor current, or speed, or power, or flow waveforms. The fundamental frequency of all of these waveforms is defined by the heart beat rate. This allows heart beat rate detection without direct ECG sensing.

Figure 3:
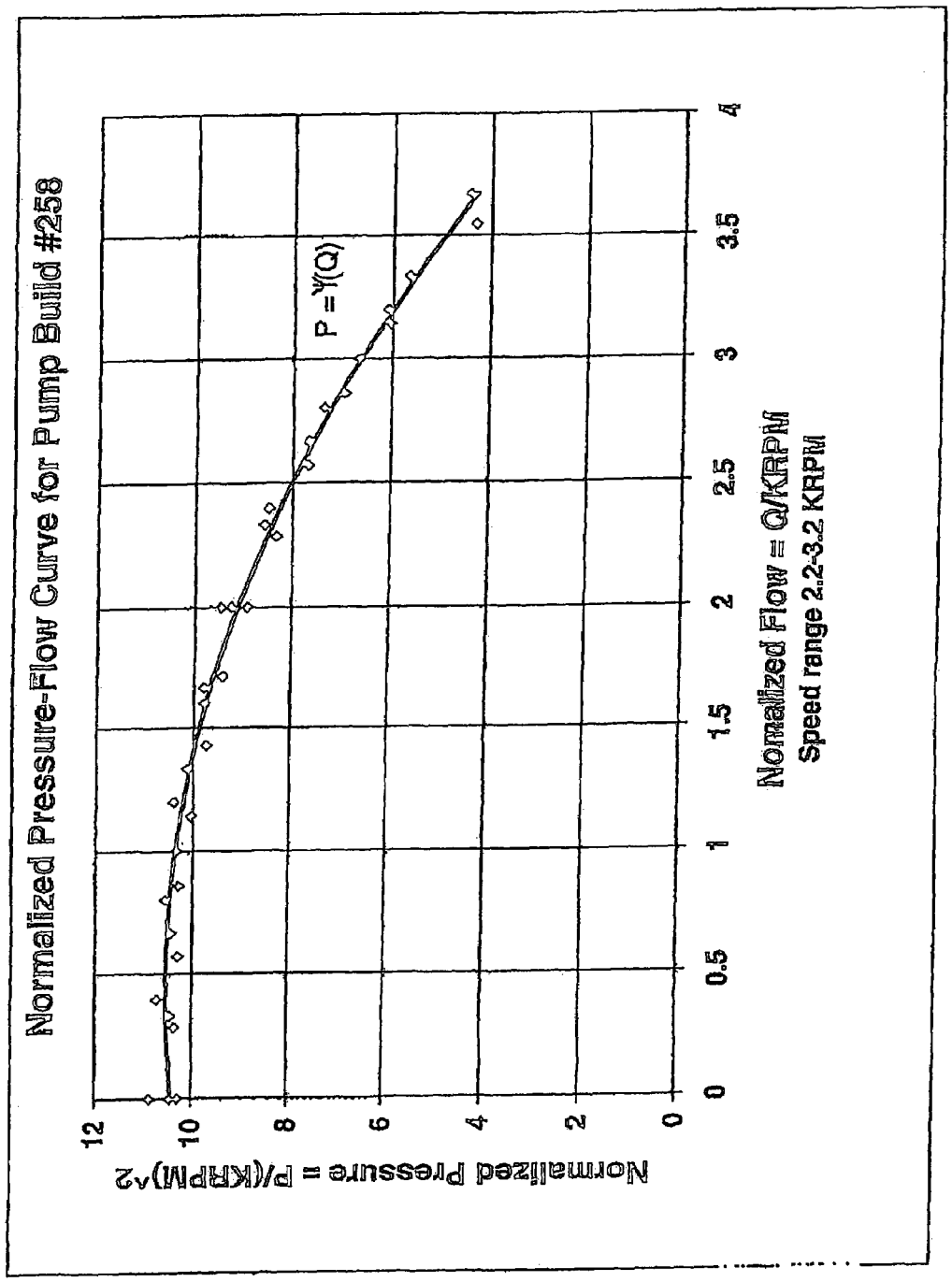
FIG. 3 is a graphical illustration of a normalized pump pressure-flow curve.

The speed waveform and the calculated pump flow waveform then are used to calculate the pump pressure drop waveform from which the maximum pressure drop across the pump is derived. The maximum pressure drop across the pump is used to estimate mean systemic pressure P. A normalized pump pressure-flow curve is used that is independent of pump operational speed:

$$P_{norm}=\psi(Q_{norm}) \quad (3)$$

where normalized pump pressure $P_{norm}=P/(\sigma*\omega^2)$, normalized flow rate $Q_{norm}=Q/\omega$, $\sigma$ is the blood density and $\omega$ is the pump rotational speed. This normalized pressure-flow dependence (FIG. 3) allows accurate pump pressure drop calculations if the pump flow and speed is known. This function can be obtained from previous bench pump test data.

The relationship between the motor power and the pump flow rate can be expressed as follows:

$$Q=\phi(S_{elec}/\omega^2) \quad (4)$$

where $S_{elec}$ is the average electrical power of the motor in time interval T, $\omega$ is the pump rotational speed, and $\phi$ is a monotonic function within the pump operating range. For a given motor-pump system $\phi$ is obtainable from pump test data using, for example, a curve fit.

Figure 4:
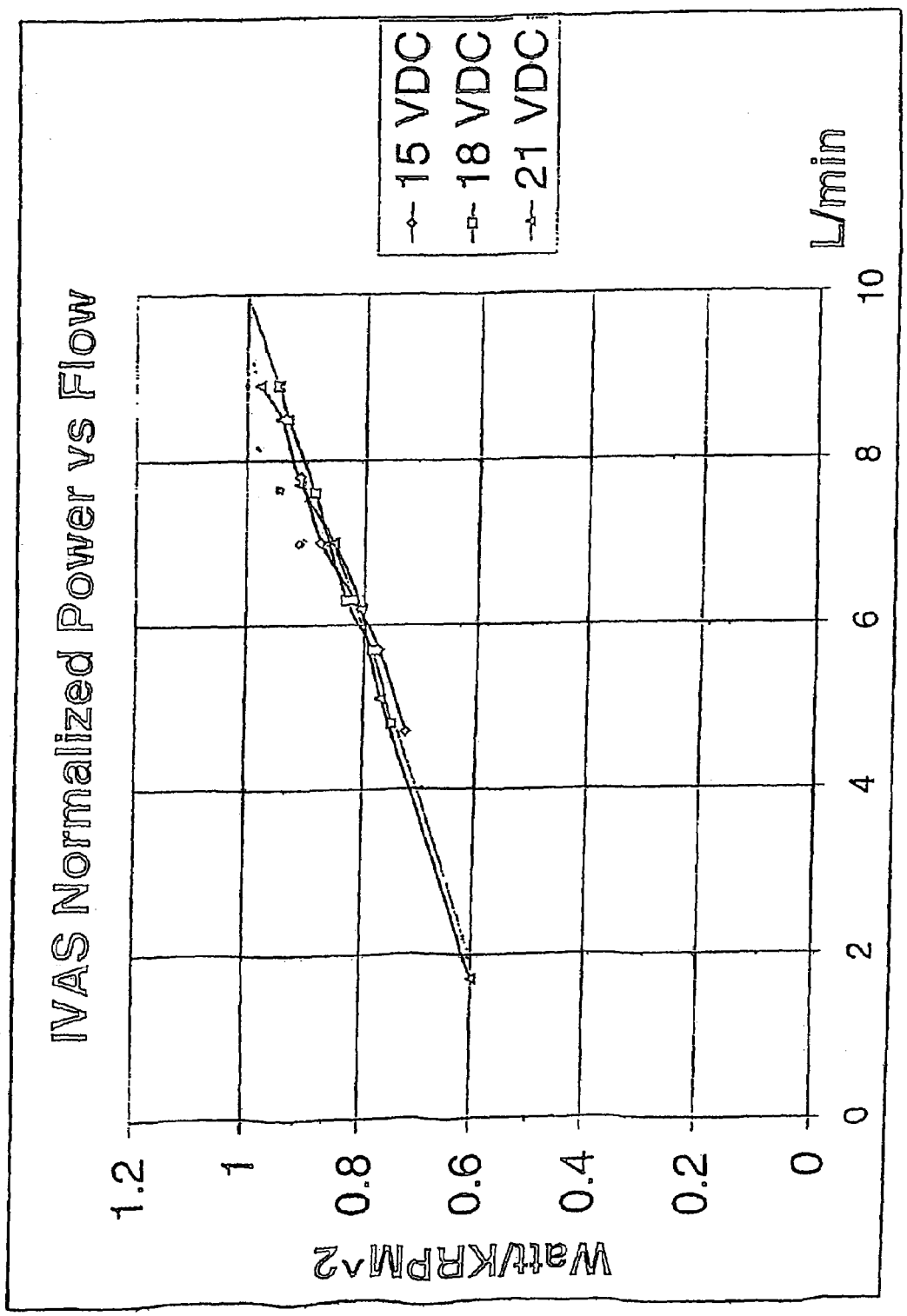
FIG. 4 is a graphical representation of normalized power plotted against flow.
Figure 5:
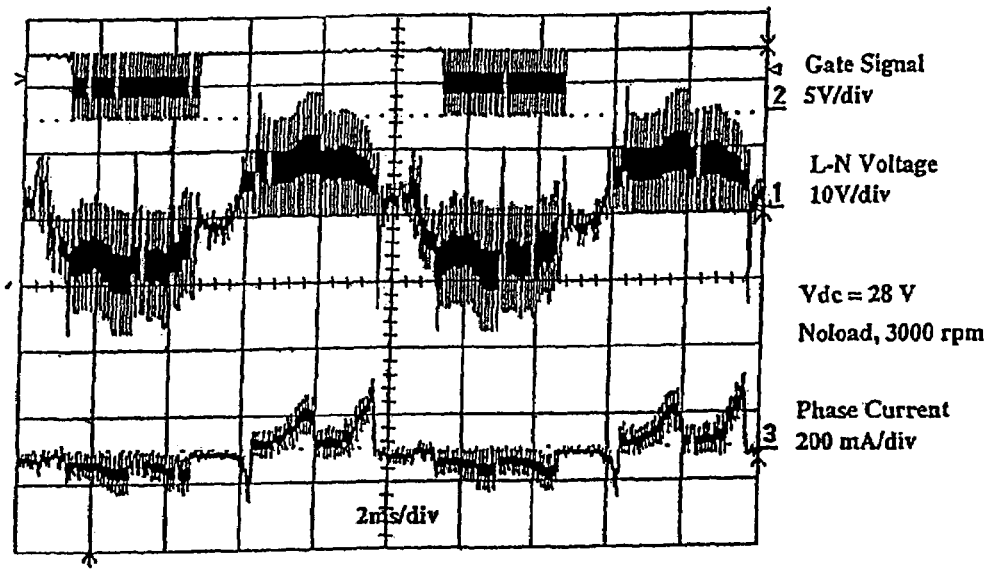
FIG. 5 is an illustration of pulse width modulation used to control motor excitation power.
Figure 5:
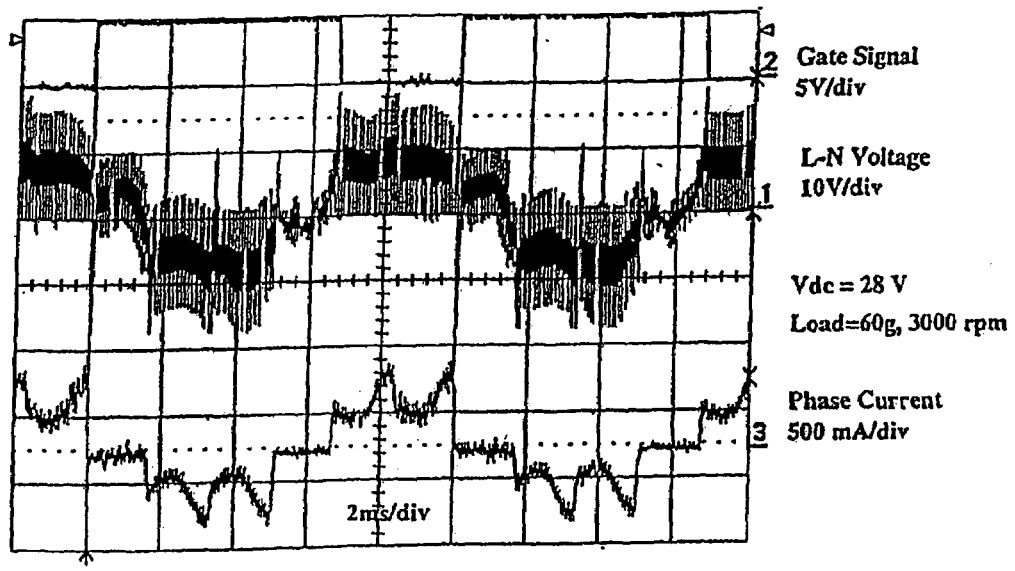

Flow versus average power relationships can be found experimentally for a variety of rotodynamic blood pumps driven by brushless DC motors having any type of phase current waveforms. For a properly designed motor-pump system this dependence is close to linear as shown in FIG. 4. However a non-linear power-flow dependence can also be derived from pump test data. This has particular advantages over previously described use of motor current and speed to derive pump flow. The method of flow calculations described in U.S. Pat. No. 5,888,242 assumes that brushless DC motor has a sinusoidal back electromotive force (EMF) and sinusoidal phase current waveforms. Most brushless DC motors do not have sinusoidal back EMF and current waveforms. Moreover, when pulse width modulation (PWM) is used to control the motor excitation power the motor phase current may be irregular and prone to spiking (FIG. 5).

The average electrical power consumed by a brushless DC motor is found by:

$$S_{elec}=v*I \quad (5)$$

where v is the motor driver bus voltage, and I is the motor average (or DC) current within a certain time interval, T.

The time interval T should be small enough to allow proper representation of the pump flow, power and speed pulsatility associated with the heart residual function. On the other hand, T should be large enough to ignore power spikes associated with the motor commutation. This defines the requirements for low-pass filter signal conditioning as well as analog to digital converter (ADC) sampling rate that is faster than 2/T samples/sec. This arrangement provides proper representation of the pump performance variation during a cardiac cycle while ignoring power disturbances associated with motor commutation and excitation power control by the PWM. In the preferred embodiment the time interval is $$120/(NP*\omega_{min}) < T < 30/HR_{max}$$

where NP is number of pump motor magnetic poles; $\omega_{min}$ is the minimum pump operating rotational frequency, RPM; $HR_{max}$ is the maximum considered patient's heart rate, BPM.

Using motor power instead of motor current (the latter was described in U.S. Pat. No. 5,888,242 by Antaki et al.) for pump flow calculation means that the calculation is independent of system voltage variations. Voltage variations that occur while LVAD systems are run on portable or implantable batteries can significantly change the current required to maintain the same pump steady state power level. Therefore, the preferred embodiment has a superior accuracy for flow calculations compared to methods that use current to calculate pump flows. This approach also eliminates the need for driver voltage regulation that is necessary if the pump flow rate is calculated using the motor current.

Figure 6:
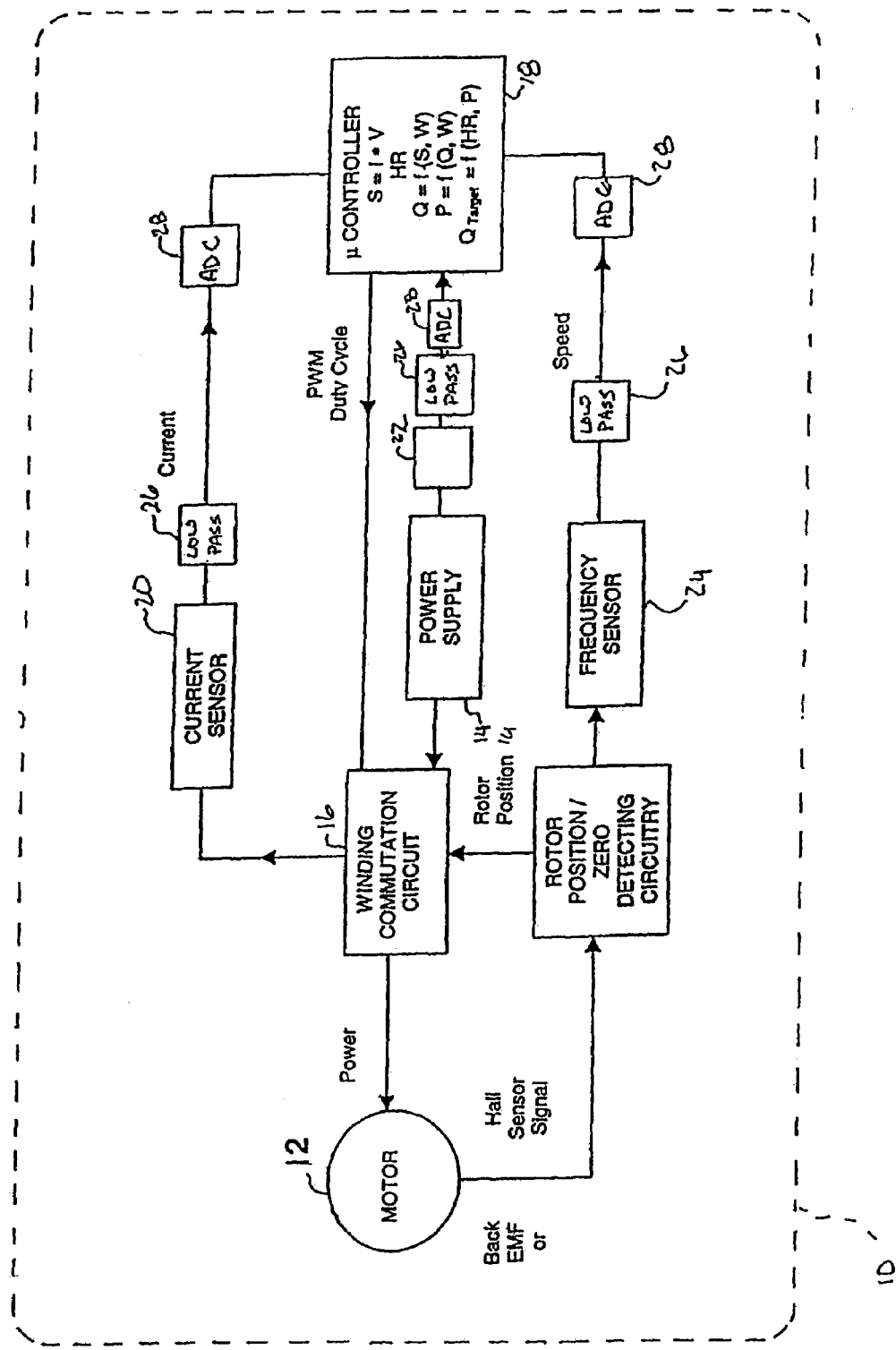
FIG. 6 is a diagrammatic illustration of a left ventricular assist device drive unit in accordance with the present invention.

With reference to FIG. 6, a blood pump 10 is driven by a brushless DC motor 12. In the preferred embodiment, the blood pump 10 is an implanted centrifugal blood pump. Alternately, mixed or axial flow blood pumps can be used. A power supply 14 supplies power to the motor 12 via a motor winding commutation circuit 16. The circuit 16 acts as a power regulator and is controlled by a microprocessor or microcontroller 18.

The microprocessor 18 receives information from three sensors. A current sensor 20 provides a current waveform to the microprocessor 18. The current waveform is the current supplied to the motor 12 by the circuit 16 over a period of time. A voltage sensor 22 provides the microprocessor 18 with a voltage waveform that represents the voltage supplied to the motor 12 over a period of time. A frequency sensor 24 supplies the microprocessor 18 with a frequency waveform that tracks the speed of the motor 12 over a period of time. Preferably, the frequency sensor 24 is a back electromotive force (EMF) or a rotor position sensor such as a Hall effect sensor that calculates a revolutions per minute (RPM) measurement to provide timing for motor winding commutation. Alternately, an optical sensor can be used to track the speed of the motor.

Within a certain time interval (e.g., every ten seconds), the microcontroller continuously receives a signal from the current sensor 20 representing mean DC motor current waveform, a signal from the frequency sensor 24 representing the pump rotational speed waveform, and a signal from the power supply representing the power supply voltage.

Based on these three inputs, the microcontroller 18 calculates a motor input power, $S_{elec}$, using equation (5); an instantaneous pump flow, Q, from equation (4); the average pump flow over the time interval; the patient heart rate HR, by counting the number of pulses in any one of the power, current, flow or speed waveforms that are associated with the residual ventricular function or by finding the waveform fundamental frequency; a pump pressure differential, P, using the pump pressure-flow relationship of equation (3) and a required or target pump flow, $Q_{target}$, for current physiologic conditions according to equation (1) or (2). The microcontroller also analyzes the pump performance and checks for predetermined patient safety conditions using power, speed, flow and pressure waveforms. Finally the microcontroller implements a change in power delivered to the motor as needed in order to first correct any detected operating conditions or if all conditions are met, to match the required flow, $Q_{target}$.

In case of a software or hardware failure associated with the microcontroller, the winding commutation circuit 16 provides uninterrupted pump performance at the predetermined (motor power) level. Thus, improved reliability is provided with this arrangement.

In the preferred embodiment, the pump motor input power is the only directly controlled parameter. By varying the pump performance through the motor power, a target pump blood flow is maintained based on the derived physiologic HR or HR/P ratio. There are, however, four functional conditions that must be met before implementing any change in motor power to achieve the target pump flow. These conditions, if not met, implement a change in motor power to correct the condition and take priority over motor power changes to achieve target flows.

The first condition is the prevention of ventricular suction. This requires an immediate pumping power reduction if either such condition or prior to the onset of such situation (a pre-suction condition) is detected.

The second condition is related to reverse flow through the pump. An instantaneous reverse flow is avoided in order to achieve proper flow circulation through the pump. If instantaneous reverse flow at any time exceeds a certain limit the controller increases pumping by delivering more power to the motor assuming that the first priority condition is satisfied.

A third condition is the microcontroller response to tachycardia or bradycardia or to errors in the HR calculation. If the calculated HR exceeded preset maximum or minimum values, the controller decreases pumping by delivering less power to the pump motor. The maximum and minimum safe HR in the preferred embodiment are 180 and 40 bpm respectively but can be adjusted to the needs of the individual patient.

The fourth condition is to ensure that pump operational speed is maintained within a predefined range for ideal system performance. The limits may depend on both patient conditions and pump technical characteristics. In the current embodiment, minimum and maximum allowable speed limits were set at 2200 RPM and 3200 RPM, respectively, but can be adjusted for individual patient needs. Any requested change in power delivered to the motor based on target flow requirements or any of the above priority conditions will not be implemented if they will cause pump speed to exceed these limits.

Prevention of ventricular suction is implemented by detection of a pre-suction condition. In the preferred embodiment, pre-suction detection is based on the assumption that low pump flow pulsatility is associated with a completely unloaded ventricle, low intraventricular pressure and steady state (nonpulsatile) systemic pressure. Any significant increase in pump flow after depulsing the circulation could lead to complete or more likely partial collapse of the ventricle wall into the pump inflow cannula orifice.

The flow pulsatility can be defined as the following:

$$DQ = (Q_{peak(+)} - Q_{mean})/Q_{mean}. \qquad (6)$$

where $Q_{mean}$ is the mean flow rate for all cardiac cycles recorded over a given control cycle and $Q_{peak(+)}$ is the average of the maximum instantaneous pump flow value within each cardiac cycle over the given control cycle. This peak flow is associated with ventricular systole when the pressure across the pump is minimal. DQ values below a predetermined limit are used to detect a pre-suction condition and require an immediate pumping power reduction.

It is understood that there are other ways to determine the pulsatility of a waveform using its extreme and mean values as well as time-based parameters. For example, the following expressions for pump flow pulsatility can also be used to detect a pre-suction conditions:

$$DQ_1 = (Q_{peak(+)} - Q_{peak(-)})/Q_{mean},$$

$$DQ_2 = (Q_{peak(+)} - Q_{peak(-)})/Q_{peak(+)},$$

$$DQ_3 = (Q_{mean} - Q_{peak(-)})/Q_{mean}, \text{ etc.}$$

where $Q_{peak(-)}$ is the average of the peak minimum instantaneous flow rates within each cardiac cycle recorded over a given control cycle. This peak minimum flow is associated with ventricular diastole when the pressure across the pump is maximum.

If suction does occur rapidly before an adequate control response based on low pulsatility limits (DQ), the pump flow will drop significantly due to inflow cannula occlusion. If the pump flow reduces below a predetermined absolute minimum flow $Q_{absmin}$, complete or significant inflow cannula occlusion is detected and requires an immediate pumping power reduction. The value of $Q_{absmin}$ is adjusted to individual patient physiology.

In the case of partial inflow cannula occlusion, the flow pulsatility may remain high, masking DQ limit detection. However, if the pump flow reduces below a predetermined relative minimum flow $Q_{rel\ min}$ expected for the current pump operating speed, partial inflow cannula occlusion is detected and again requires an immediate pumping power reduction. The relative minimum flow $Q_{rel\ min}$ expected for any current pump operating speed is defined as the following:

$$Q_{rel\ min} = A^*(\omega - \omega_0)^n \quad (7)$$

In the preferred embodiment, A=1.5, $\omega_0$=1.2 KRPM, n=2, but can be different. If at any given speed within the controller allowed range, the pump flow $Q<Q_{rel\ min}$ the controller reduces power to the motor until the flow is restored to $Q>Q_{rel\ min}$.

An additional indicator of either a suction or a pre-suction condition is the absolute value for flow pulsatility defined as the following:

$$absDQ = (Q_{peak(+)} - Q_{peak(-)})$$

where $Q_{peak(+)}$ and $Q_{peak(-)}$ are the average of the peak maximum and peak minimum instantaneous flow rates within each cardiac cycle recorded over a given control cycle. Any absDQ values below a predetermined limit, can be used to detect such conditions and require an immediate pumping power reduction.

The preferred embodiment requires three input variables: motor current waveform, motor speed waveform and power source (driver) voltage, from which motor power, pump flow, ventricular contraction rate and systemic pressure are determined. This removes the technical and reliability problems associated with direct flow, pressure and heart rate sensing. The motor speed output is available in most brushless DC (BLDC) motor drivers; motor current and power supply voltage sensing are also performed within the driver. This brings all required sensing inside the motor controller/driver and simplifies the system configuration significantly. It is to be appreciated that the preferred embodiment is independent of the motor control mode: the motor speed and current as well as the driver voltage may vary during a cardiac cycle or remain constant.

In the preferred embodiment, the current, voltage and speed waveforms are employed to find the heart rate, motor power, mean pump flow and systemic pressure. Therefore the waveform acquiring interval has to be long enough to determine the heart rate and the average pump flow. Assuming that the normal heart rate is unlikely to be less than 60 BPM, a 6-to-12 second time interval for speed, current and voltage waveform recording is reasonable. This is also adequate to meet a required physiologic dynamic response of a patient to changing heart rate, preload and afterload conditions.

Because the instantaneous maximum and minimum peak pump flows have to be calculated using the sensed voltage, current and speed waveforms, signal noise may lead to unacceptable errors which result in improper system functioning. In the preferred embodiment, waveform filtering with low-pass filters 26 is performed on each of the three waveforms before being digitized by analog to digital converters 28 for analysis by the microprocessor 18.

Figure 7:
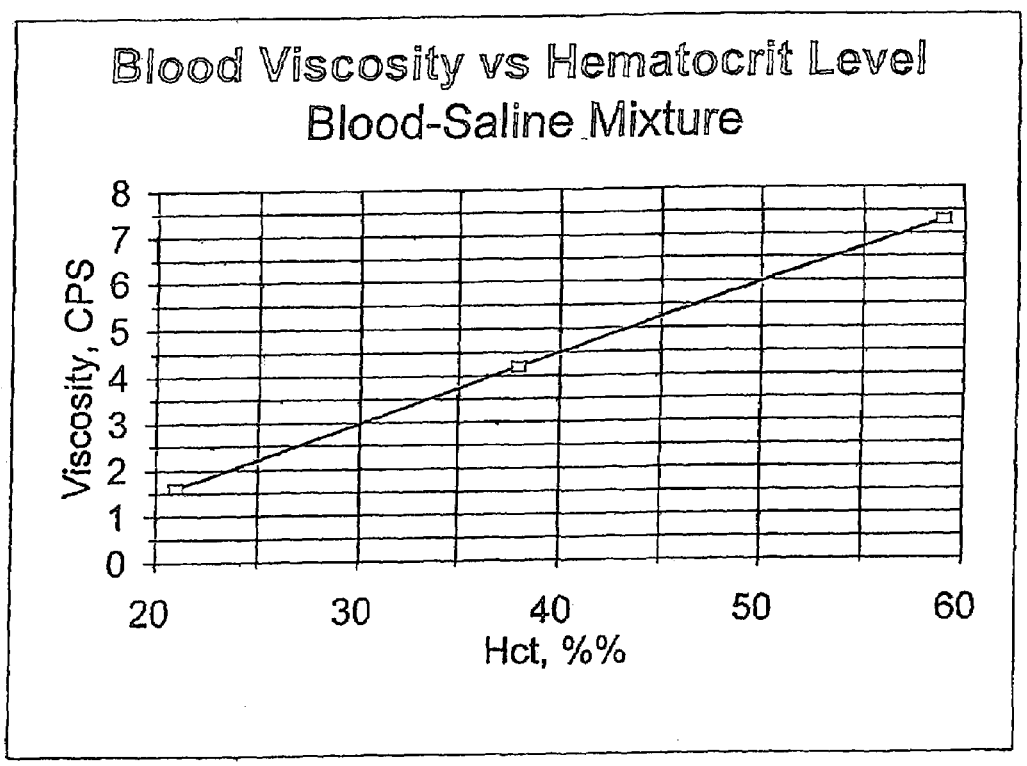
FIG. 7 is a graphical representation of blood viscosity versus hematocrit level.

Derived from equation 4, the steady state power-flow curves can be used for mean, peak, and minimum pump flow calculations. The accuracy of the pump flow calculation using equation (4) is affected by blood viscosity changes. The blood viscosity depends on blood hematocrit level (FIG. 7). As blood viscosity increases, more motor power is required for pumping at the same blood flow rate. Therefore, for accurate pump flow calculations a correction factor $C_h$ can be added to expression (4):

$$Q = \phi(S/\omega 2) + Ch$$

A correction factor such as a 0.1 L/min per each percent of hematocrit change from a baseline is preferred.

Since the instantaneous pump flow is known, the pump inlet-outlet pressure difference waveform is calculated using the normalized pressure-flow curve (3). The estimated mean systemic arterial pressure is derived as the maximum pump inlet-outlet pressure difference, P and is defined as:

$$P = \max\{P_{norm} * \omega^n\} \quad (8)$$

This estimate of systemic arterial pressure is used to calculate (M=HR/P) and then the required pump flow $Q_{target}$ is calculated using equation (2).

As discussed above, a patient heart rate can be obtained by performing a harmonic analysis, a fast Fourier transform or equivalent analysis, on the motor current waveform. The waveform fundamental frequency corresponds to the heart rate. The required pump flow $Q_{target}$ is calculated using equation (1) or (2).

After the mean pump flow ($Q_{mean}$) is calculated, the flow pulsatility (DQ) as in equation (6) is found. Also the error between the actual pump flow and the required flow, $Q_{target}$ can be calculated as:

$$\Delta Q = (Q_{Target} - Q_{mean})/Q_{mean} \quad (9)$$

Figure 8:
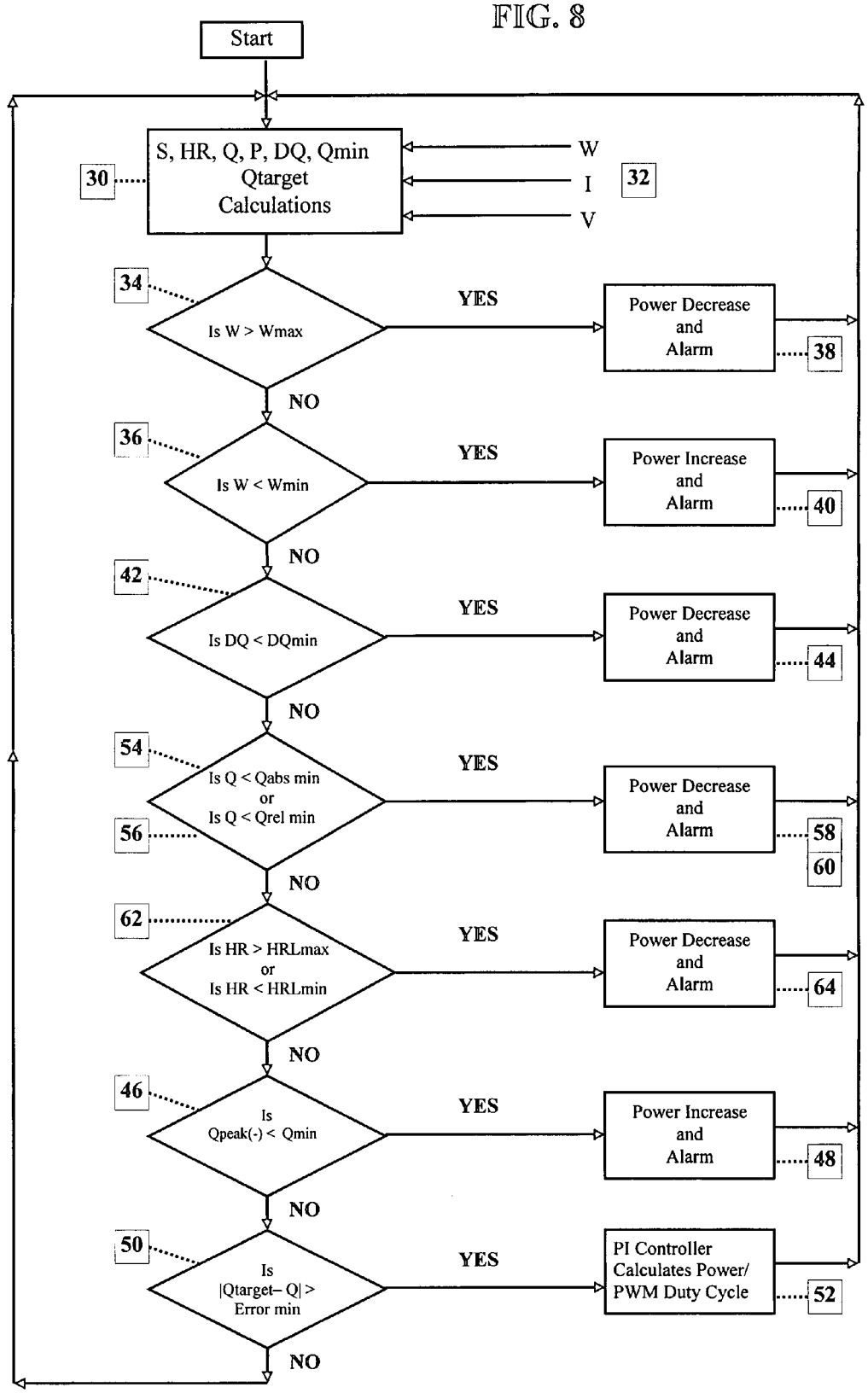
FIG. 8 is a flow diagram of safety checks that prioritizes emergency conditions.

Since all necessary parameters—$Q_{mean}$, $Q_{peak}$, $Q_{min}$, AbsDQ, DQ, $\Delta Q$, and $Q_{target}$ are calculable, logic analysis is performed and a power control signal is produced for each data acquisition interval of six to twelve seconds in the preferred embodiment. With reference to FIG. 8, the logic analysis starts with the calculations 30 of power, heart rate, flow, pressure, pulsatility, minimum and maximum peak flow, and target flow from the received frequency ($\omega$), current (I), and voltage (V) waveforms 32. The calculated data is then analyzed to see if any of a set of four priority conditions are not met. First, the speed of the motor is monitored to be sure it is within derived parameters 34, 36. If it is greater then the set maximum, $\omega_{max}$, then the power is decreased at step 38 and an alarm may be provided. If the frequency is less than the minimum $\omega_{min}$ power is increased at step 40 and, again, an alarm may be provided.

Second, pulsatility DQ is checked to make sure it is not less than a preset limit $DQ_{min}$ indicating onset of inflow cannula suction at step 42. If it is, then power is decreased as represented at step 44 and an alarm may be triggered. Next, the flow rate is compared to the absolute and relative minimum flow rates for a given speed 54, 56. If $Q<Q_{abs\ min}$ or $Q<Q_{rel\ min}$, then suction is detected, power decreased and an alarm can be actuated 58, 60.

Third, the calculated HR is compared to maximum and minimum limits for arrhythmia or fibrillation detection 62. If HR is out of preset limits then power is decreased as represented in step 64 an alarm can be actuated.

Fourth, peak minimum flow rate is compared to a predetermined maximum allowable reverse pump flow 46. If $Q_{peak(-)}<Q_{min}$, then power is increased as indicated in the flow chart at 48 and an alarm may be actuated.

Finally, if all of the above priority conditions are met, then the power to the motor can be changed to achieve the target flow based on the relative difference between the actual pump flow and the required flow, $\Delta Q$ 50, 52. If any of the above conditions were not met, then any associated change in pump power level to correct the condition takes priority over that to achieve the target flow, and the control loop begins again.

It is to be understood that additional safety and control conditions can also be utilized in the proposed system. For example, if the motor power level is outside of a predetermined range, an alarm signal is initiated and the system is switched to a safety mode.

The physiologic control algorithm of the present invention uses a "sensorless" approach, i.e., no pressure or flow sensors, and no ECG signal is required. The pump speed, motor voltage, and current waveforms are used for heart rate, pump flow, and patient pressure estimates. The controller analyzes this information and develops a control signal targeting a pump flow that is appropriate to the patient condition. This pump flow is a predetermined function of the patient pressure and/or heart rate and also depends on the size and degree of heart failure of the patient. Several limiting safety conditions and correction factors are involved in the control signal development.

Several significant advantages are attained relative to known arrangements.

First, using the pump flow instead of the pump speed as the control objective advantageously provides a responsive and flexible control system that can automatically adjust the pump performance according to changing patient condition (i.e., enhanced left ventricle contractility due to the heart recovery). This also eliminates the need for the speed stabilizing circuitry (speed control loop) in the motor drive since the speed may vary during the cardiac cycle.

Second, the developed algorithm is applicable to a wide variety of brushless motors driven by currents having waveforms of any shape, rather than being limited to a sine-wave current type of motor. This is advantageous since most brushless motors are not of this type.

Third, the present control algorithm avoids the potentially dangerous situation of ventricular collapse by detecting conditions which precede that event, as opposed to incrementing pump speed until such a situation is detected as suggested by others.

Fourth, the control methodology of the present invention also simplifies the control system by eliminating the need for speed stabilizing circuitry and voltage regulating circuitry.

Fifth, in addition, the control method disclosed herein is independent of voltage variations that can be significant when the pump is powered by batteries.

Sixth, still further, the present control arrangement is deemed more accurate and consequently safer for patients since it recognizes and takes into account patient blood viscosity variations and is also independent of blood flow inertia.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A cardiac assist apparatus comprising:
   a blood pump;
   a drive unit that drives the blood pump;
   a power supply that supplies power to the drive unit;
   a frequency sensor that senses a rotational speed of the blood pump;
   a current sensor that senses an average direct current waveform of the drive unit;
   a power supply voltage sensor that senses a power supply voltage; and
   a blood pump controller that;
   (i) receives data from the frequency sensor, current sensor, and the power supply voltage sensor;
   (ii) passively determines, from said data, a physiologic status of a patient without affecting one or more of the following: the pump's performance and the patient's physiology, the patient's physiologic status comprising one or more of the following: a drive unit input power for determination of pump flow rate; a heart rate; a pump flow rate; and, a pressure differential; and
   (iii) calculates a target flow based on the physiologic status; and
   (iv) automatically adjusts the blood pump to the target flow.

2. The cardiac assist apparatus as set forth in claim 1, wherein the controller estimates a drive unit input power, a flow rate, a patient heart rate, pressure and the target flow rate.

3. The cardiac assist apparatus as set forth in claim 1, further comprising a drive unit winding commutation circuit for relaying the target flow to the drive unit motor.

4. The cardiac assist apparatus as set forth in claim 1, wherein the drive unit includes a brushless DC motor.

5. The cardiac assist apparatus as set forth in claim 1, wherein the power supply includes at least one rechargeable battery.

6. The cardiac assist apparatus as set forth in claim 1, wherein the frequency sensor includes one of a back EMF, Hall and optical sensor.

7. The cardiac assist apparatus as set forth in claim 1, wherein the patient's physiological status is a heart rate, and the blood pump controller calculates the target pump flow rate based on the determined heart rate.

8. The cardiac assist apparatus as set forth in claim 7, wherein the target flow rate is within a pre-determined margin.

9. The cardiac assist apparatus as set forth in claim 8, wherein the margin comprises flow rates corresponding to preset maximum and minimum heartbeats per minute.

10. A method of controlling blood flow with a blood pump comprising the steps of:
- sensing a current waveform of a drive motor of the blood pump;
- sensing an input voltage waveform to the drive motor;
- sensing a rotational frequency waveform of the drive motor;
- passively determining, at a blood pump controller, a physiologic status of a patient based on one or more of the sensed current waveform, input voltage waveform, and rotational frequency waveform, the patient's physiologic status comprising one or more of the following: a drive motor input power of pump flow rate; a heart; a pump flow rate; and, a pressure differential wherein said step of determining is performed without affecting one or more of the following: the pump's performance and the patient's physiology; and
- calculating a target flow based on the physiologic status; and
- automatically adjusting the blood pump to the target flow.

11. The method as set forth in claim 10, further comprising the step of analyzing the pump's performance to verify that the pump is operating within predetermined conditions.

12. The method as set forth in claim 10, wherein the predetermined conditions comprise one or more of the following: a minimum flow rate; a maximum flow rate; a minimum pulsatility; a minimum pump rotational speed; and, a maximum pump rotational speed.

13. The method as set forth in claim 12 wherein the predetermined conditions comprise one or more of the following: absolute minimum flow rate, and relative minimum flow rate.

14. The method as set forth in claim 13 further comprising the step of calculating the relative minimum flow rate as $Q_{rel\,min} = A*(\omega - \omega_0)n$ wherein A, n and $\omega_0$ are constants and $\omega$ is the pump rotational speed.

15. The method as set in claim 13, further comprising the step of reverting to a pre-selected default power level decrease in response to detecting ventricular suction.

16. The method as set forth in claim 10, wherein the motor input power is calculated using the equation:

$$S_{elec} = v*I$$

where $S_{elec} = v*I$ is an average electrical power of the motor in a time interval T, v is the measured voltage, and I is an average current over the time interval I.

17. The method as set forth in claim 16, wherein the patient's physiologic status is a heart rate, the step of calculating the heart rate comprises analyzing one or more of the following for a fundamental frequency: the current waveform, input power, rotational frequency, pressure differential and pump flow waveform.

18. The method as set forth in claim 10, wherein the pump pressure differential P is calculated using the equation:

$$P_{norm} = \psi(Q_{norm})$$

where normalized pump pressure $P_{norm} = P/(\sigma*\omega 2)$, normalized flow rate $Q_{norm} = Q/\omega$, and $\omega$ is the pump rotational speed, $\sigma$ is the blood density.

19. The method as set forth in claim 10, wherein the target pump flow is calculated using one of the following equations:

$$Q_{target} = C_1 * HR + C_2; \text{ and,}$$

$$Q_{target} = f(M);$$

where $Q_{target}$ is the desired flow rate, $C_1$ and $C_2$ are constants determined by patient heart condition and size, M=HR/P where P is the pressure and HR is the heart rate.

20. The method as set forth in claim 10, wherein the step of calculating the target pump flow further comprises the step of tracking the patient's heart rate and basing the flow rate on the heart rate.

21. The method as set forth in claim 10, further comprising the step of reverting to a pre-selected default pump rotational speed in the event of a controller failure.

22. The method as set forth in claim 10, further comprising the step of reverting to a pre-selected default motor input power in the event of a controller failure.

23. The method as set forth in claim 10, further comprising the step of reverting to a pre-selected default PWM duty cycle in the event of a controller failure.

24. The method as set forth in claim 10, wherein the pump flow is calculated using the equation:

$$Q = \phi(S/\omega^2)$$

where S=V*I, S is average electrical power, V is motor driven bus voltage, I is motor average current within a certain time interval, Q is pump flow, and $\omega$ is the pump rotational speed.

* * * * *